US012599711B2

(12) United States Patent
Katakowski et al.

(10) Patent No.: US 12,599,711 B2
(45) Date of Patent: Apr. 14, 2026

(54) DEVICE AND METHOD OF ISOLATING EXTRACELLULAR VESICLES

(71) Applicant: FOREVER LABS, INC., Ann Arbor, MI (US)

(72) Inventors: Mark Katakowski, Ann Arbor, MI (US); Ann Hozeska-Solgot, Rochester, MI (US)

(73) Assignee: FOREVER LABS, INC., Ann Arbor, MI (US)

( * ) Notice: Subject to any disclaimer, the term of this patent is extended or adjusted under 35 U.S.C. 154(b) by 728 days.

(21) Appl. No.: 17/893,846

(22) Filed: Aug. 23, 2022

(65) Prior Publication Data

US 2023/0060145 A1     Mar. 2, 2023

Related U.S. Application Data

(60) Provisional application No. 63/236,643, filed on Aug. 24, 2021.

(51) Int. Cl.
*A61M 1/36*          (2006.01)
*B01D 21/26*         (2006.01)

(52) U.S. Cl.
CPC ......... *A61M 1/3693* (2013.01); *B01D 21/262* (2013.01); *A61M 2202/0415* (2013.01); *A61M 2202/0427* (2013.01)

(58) Field of Classification Search
CPC ........ A61M 1/3693; A61M 2202/0415; A61M 2202/0427; A61M 1/029; B01D 21/262; B01D 17/0217; B01D 21/26
USPC ......... 210/360.1, 787, 380.1, 781, 782, 788, 210/382, 789; 422/72, 533, 548, 68.1
See application file for complete search history.

(56) References Cited

U.S. PATENT DOCUMENTS

| | | | |
|---|---|---|---|
| 3,583,627 | A | 6/1971 | Wilson |
| 10,351,813 | B2 | 7/2019 | Johnson et al. |
| 11,129,930 | B2 | 9/2021 | Esteron |
| 2002/0185457 | A1 | 12/2002 | Smith et al. |

(Continued)

FOREIGN PATENT DOCUMENTS

| | | |
|---|---|---|
| EP | 2343132 B1 | 9/2017 |
| EP | 3230433 B1 | 8/2021 |

OTHER PUBLICATIONS

PCT App. No. PCT/US22/41168; International Search Report and Written Opinion mailed Jan. 19, 2023.

*Primary Examiner* — Magali P Slawski
*Assistant Examiner* — Bernadette Karen McGann
(74) *Attorney, Agent, or Firm* — MARSHALL, GERSTEIN & BORUN LLP

(57)          ABSTRACT

A centrifugal device includes a container having a body with a first end and a second end disposed opposite to the first end. A cap is coupled to the second end of the container, and the cap includes a top surface having at least one port configured to receive or transmit one or more of air or fluid. So configured, the container is moveable between an upright position, in which a first fluid disposed in the container is centrifuged to precipitate at least one extracellular vesicle separate from the first fluid, and an inverted position in which one or more of the first fluid having at least one extracellular vesicle depleted therefrom is removed from the container and a second fluid mixed with the at least one extracellular vesicle removed is withdrawn from the container for injection.

17 Claims, 7 Drawing Sheets

(56)     References Cited

U.S. PATENT DOCUMENTS

| | | |
|---|---|---|
| 2004/0052682 A1 | 3/2004 | Yokoi et al. |
| 2004/0147386 A1 | 7/2004 | Grumberg et al. |
| 2007/0208321 A1 | 9/2007 | Leach et al. |
| 2010/0125236 A1 | 5/2010 | Bare et al. |
| 2012/0015796 A1 | 1/2012 | Leach et al. |
| 2012/0053041 A1 | 3/2012 | Ihm et al. |
| 2015/0023939 A1 | 1/2015 | Woodell-May |
| 2016/0160173 A1 | 6/2016 | Johnson et al. |
| 2017/0247744 A1 | 8/2017 | Mitsuhashi et al. |
| 2019/0231692 A1* | 8/2019 | Katakowski ......... A61K 9/0019 |
| 2019/0336646 A1 | 11/2019 | Peled et al. |
| 2020/0009304 A1 | 1/2020 | Dorian et al. |
| 2020/0009312 A1 | 1/2020 | Min et al. |
| 2020/0009553 A1 | 1/2020 | Roth |
| 2020/0171485 A1 | 6/2020 | Heinrich |
| 2020/0179827 A1 | 6/2020 | Deregibus et al. |
| 2020/0215243 A1 | 7/2020 | Dorian et al. |
| 2020/0297761 A1 | 9/2020 | Ding et al. |
| 2021/0236428 A1 | 8/2021 | Katakowski et al. |

* cited by examiner

FIG. 3E                    FIG. 3F

PRP + EVF READY FOR INJECTION

ADD PLASMA +
SUPER SHOT
SOLUTION

CENTRIFUGE

EV + PRP
FRACTION

PLATELET-RICH FRACTION
+ EV FRACTION

INVERT

REMOVE DEPLETED
PRP + SUPERSHOT
SOLUTION

READY FOR INJECTION

PRP + EV
(SUPERSHOT PRP)

DEVICE AND METHOD OF ISOLATING EXTRACELLULAR VESICLES

CROSS-REFERENCE TO RELATED APPLICATION

This application is a U.S. non-provisional patent application, which claims the benefit of and priority to U.S. Provisional Patent Application No. 63/236,643 filed on Aug. 24, 2021, the entire disclosure of which is incorporated herein by reference.

TECHNICAL FIELD

This disclosure relates to cell isolation methods and devices and, in particular, to a device and method for rapid isolation of extracellular vesicles.

BACKGROUND

Extracellular vesicles (such as exosomes) are released by cells that efficiently transfer their molecular cargo to other cells. The therapeutic effects of extracellular vesicles derive from their cargo (such as miRNAs, other non-coding RNAs, and proteins) and surface molecules. In addition, extracellular vesicles can be functional components of the extracellular matrix that participate in organization, cell-regulation, and determining the physical properties of connective tissues and bone.

Injections of platelet rich plasma (PRP) and bone marrow concentrate (BMC) are used in clinical applications to promote healing, stimulate tissue regrowth, vascularize, ameliorate inflammation, and rejuvenate uninjured endogenous tissue. Extracellular vesicles are found in all biofluids, including the blood and marrow, and have been demonstrated to confer many of the effects of the cells that they are produced by. For example, extracellular vesicles from umbilical cord or bone marrow MSCs have been demonstrated to stimulate rejuvenation of human skin, or improve the survival of transplanted fat grafts. It has been demonstrated that extracellular vesicles from bone mesenchymal stem cells exerted similar chondroprotective and anti-inflammatory function and protected mice from developing osteoarthritis, suggesting that extracellular vesicles reproduce the main therapeutic effect of the MSCs. Indeed, recent scientific and clinical evidence suggests that MSCs may not primarily exert their therapeutic functions in a cellular, but rather in a paracrine manner; extracellular vesicles (such as exosomes and microvesicles) have been identified as major mediators of these paracrine effects. Extracellular vesicles isolated from fluids, such as biofluids, have also been employed for diagnostic purposes, as their contents may reflect injury, infection, cancer, immune dysfunction, or other pathologies.

Due to their low density and small size, extracellular vesicles are commonly isolated by filtration, ultra-centrifugation, immunoaffinity, microfluidics, or polymeric precipitation. Current devices employed to partition blood or bone marrow (into fractions such as red blood cells (RBCs), platelet poor plasma (PPP), and bone marrow concentrate (BMC) or PRP) use low-speed centrifugation, and extracellular vesicles are not effectively isolated or concentrated into one partition. Thus, devices that concentrate whole blood or bone marrow are not concentrating the biological agents, such as extracellular vesicles that are likely to be delivering a substantial portion of the therapeutic effect.

In addition, platelet-rich plasma (PRP) is a preparation for therapeutic purposes that is also increasingly accepted for various musculoskeletal disorders, would healing, cosmetics, and regenerative medicine due at least to its theoretical potential to repair tissues. PRP therapy uses injection of the patient's own platelets. As described, platelets are concentrated by centrifugation from aperipheral blood draw resulting in three fractions: RBCs, PPP and PRP.

In a standard PRP procedure, the PRP fraction is injected leaving biological molecules such as extracellular vesicles to be discarded with the PPP. Extracellular vesicles mediate a series of cellular functions such as the transport of materials and intercellular communication. Thus, increasing the concentration of extracellular vesicles in PRP may improve the PRP therapeutic effect.

SUMMARY OF THE DISCLOSURE

In accordance with one exemplary aspect of the present disclosure, a centrifugal device comprises a container having a body with a first end and a second end disposed opposite to the first end. A cap is coupled to the second end of the container, and the cap includes a top surface having at least one port configured to receive or transmit one or more of air or fluid. So configured, the container is moveable between an upright position, in which a first fluid disposed in the container is centrifuged to precipitate at least one extracellular vesicle separate from the first fluid, and an inverted position. The inverted position is a position in which one or more of the first fluid having at least one extracellular vesicle depleted therefrom is removed from the container and a second fluid mixed with the at least one extracellular vesicle removed is withdrawn from the container for injection.

According to another aspect of the present disclosure, a method of isolating extracellular vesicles from a fluid comprises adding an aqueous two-phase solution and a first fluid to a container of a centrifugal device, the container in an upright position. The method also includes centrifuging the aqueous two-phase solution and the first fluid in the container to form a fraction of extracellular vesicles disposed near a first end of the container separate from the first fluid. The method still further includes moving the container of the centrifugal device from an upright position to an inverted position and removing the first fluid with extracellular vesicles depleted therefrom from the container through at least one port of the container. The method still also includes moving the container back to the upright position and adding a second fluid to the container. The method still further includes mixing the second fluid with the fraction of extracellular vesicles disposed near the first end of the container. The method also includes moving the container back to the inverted position and removing the second fluid with the fraction of extracellular vesicles through the at least one port of the container for injection.

According to another aspect of the present disclosure, another centrifugal device comprises a container having a body with a first end and a second end disposed opposite to the first end. A cap is coupled to the second end of the container, and the cap includes a top surface having a port configured to receive or transmit one or more of air or fluid. In addition, a Y-connector is coupled to the port of the cap and has a first port for receiving or transmitting air and a second port for receiving or transmitting fluid. So configured, the container is moveable between an upright position, in which a first fluid and an aqueous two-phase solution disposed in the container is centrifuged to precipitate at least one extracellular vesicle, and an inverted position. The inverted position is a position in which one or more of the first fluid having at least one extracellular vesicle depleted therefrom is removed from the container through the second port and a second fluid is mixed with the at least one extracellular vesicle is removed from the container through the second port for injection.

According to another aspect of the present disclosure, a method of isolating extracellular vesicles from a fluid comprises transferring a first volume of plasma from a transfer device to a container of a centrifugal device, maintaining a second volume of plasma in the transfer device, and adding an aqueous two-phase solution to the container of the centrifugal device. The method also includes centrifuging the aqueous two-phase solution and the plasma in the container to form a fraction of extracellular vesicles and platelet-rich plasma, and inverting the container of the centrifugal device and removing remaining aqueous two-phase solution and depleted platelet-poor plasma from the container. The method still further includes moving the container from an inverted position back to an upright position and adding the second volume of plasma from the transfer device into the container of the centrifugal device. The method also includes resuspending the fraction of extracellular vesicles and platelet-rich plasma with the second volume of plasma in the container by one or more of shaking, inverting, vortexing, and/or centrifuging the container; and lastly, inverting the container and removing platelet-rich plasma with extracellular vesicles for placement in an injection device, the volume of platelet-rich plasma and extracellular vesicles equal to the second volume of plasma in the transfer device.

In further accordance with any one or more of the exemplary aspects, the device for isolating extracellular vesicles or any method of the present disclosure may include any one or more of the following preferred forms.

In some aspects, the at least one port may include a first port configured to receive or transmit air and having a filter, and a second port may be configured to receive or transmit fluid.

In another aspect, one or both of the first and second ports may include one or more of a removable cap and a luer lock connection configured to be coupled to a syringe.

In yet another aspect, the at least one port may include a single port, and the device may further comprise a Y-type connector one of fixedly or removably coupled to the single port. The Y-type connector may include a first port configured to receive air and including a filter, and a second port having a syringe fitting configured to be coupled to a syringe, such that when the container is in the inverted position, air flows into the first port and the fluid having depleted extracellular vesicles flows out of the second port.

In another aspect, the container may be is cylindrical in shape, such as a tube, and the first end may include a tapered portion, and the second end may include an open portion.

In other aspects, the device may include at least one tube disposed within the at least one port and extending into an internal area of the container, and the at least one tube may be configured to aid in the addition or removal of fluid to or from the container.

In still other examples, one or more of: (1) the container may be configured to receive platelet-poor plasma and an aqueous two-phase solution, and the aqueous two-phase solution may be a concentrated aqueous two-phase solution including a concentrated polyethylene glycol-dextran (PEG- DEX) solution; (2) the first fluid may be a platelet-poor plasma; and (3) the second fluid may be a platelet-rich plasma.

In still other examples, the first fluid may be one of a biofluid or other possible reconstituting fluid. In addition, the second fluid may be one of a biofluid, a sterile solution such as saline, or other possible reconstituting fluids.

In still other aspects, wherein the centrifugal device may be a first centrifugal device, and, before transferring the first volume of plasma from the transfer device to the container of the first centrifugal device, the method may further comprise adding whole blood to a container of a second centrifugal device, centrifuging the whole blood, and removing the red blood cells from the container of the second centrifugal device.

In another example, the method may further comprise transferring plasma from the container of the second centrifugal device to the transfer device after removing the red blood cells from the container of the second centrifugal device.

Additional optional aspects and features are disclosed, which may be arranged in any functionally appropriate manner, either alone or in any functionally viable combination, consistent with the teachings of the disclosure. Other aspects and advantages will become apparent upon consideration of the following detail description.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the example embodiments, except as may be explicitly delineated in the corresponding written description. Also, none of the drawings is necessarily to scale.

FIGS. 3A-3G depict steps of a method of isolation of extracellular vesicles according to another aspect of the present disclosure;

DETAILED DESCRIPTION

Generally, a centrifugal device, system and method for rapid isolation of a fraction of extracellular vesicles from plasma, which could be used in the preparation of platelet rich plasma, is disclosed.

Figure 1:
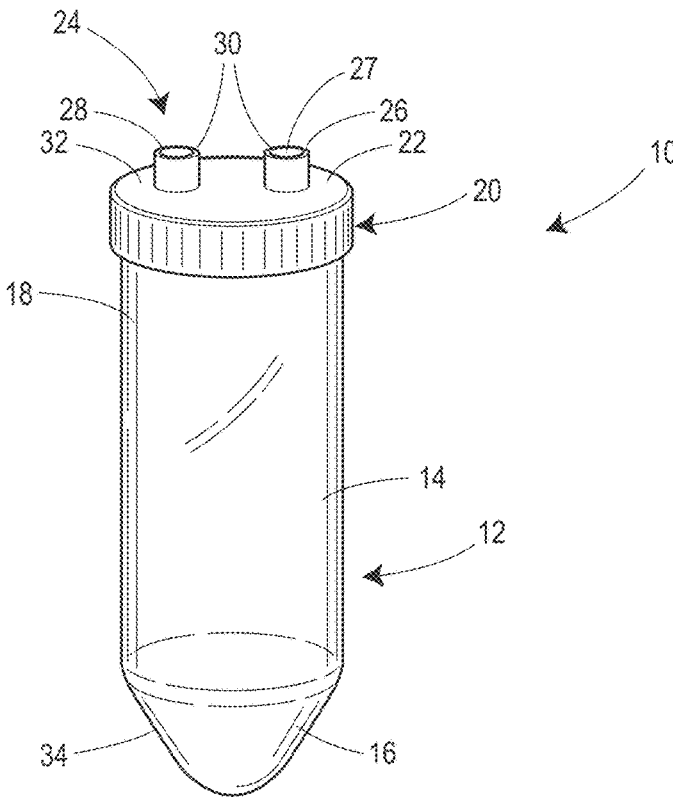
FIG. 1 is a front, perspective view of a centrifugal device according to one aspect of the present disclosure.

Referring now to FIG. 1, a centrifugal device 10 according to one aspect of the present disclosure is depicted. The centrifugal device 10 includes a container 12, which may take the form of a tube and/or be cylindrical in shape. The container 12 includes a body 14 having a first end 16 and a second end 18 disposed opposite to the first end 16. A cap 20 is removably coupled to the second end 18 of the container 12 and includes a top surface 22 having at least one port 24 configured to receive or transmit one or more of fluid, such as a biofluid, fluid other than a biofluid, or air, as explained more below. The cap 20 may be circular, partially circular in shape, or have any other geometry or shape that aids in the withdrawal of fluid, as explained more below, and still fall within the scope of the present disclosure.

Figure 3A:
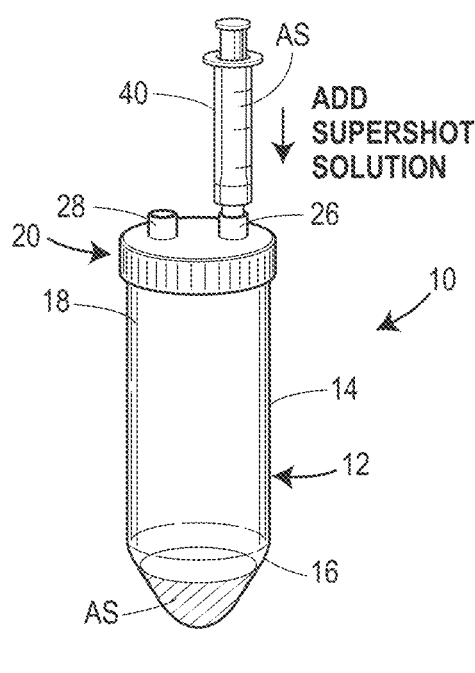
Figure 3B:
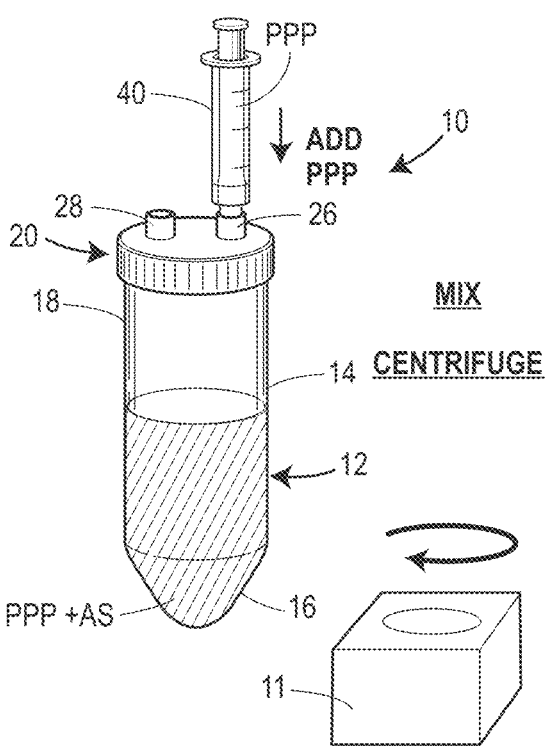
Figure 3C:
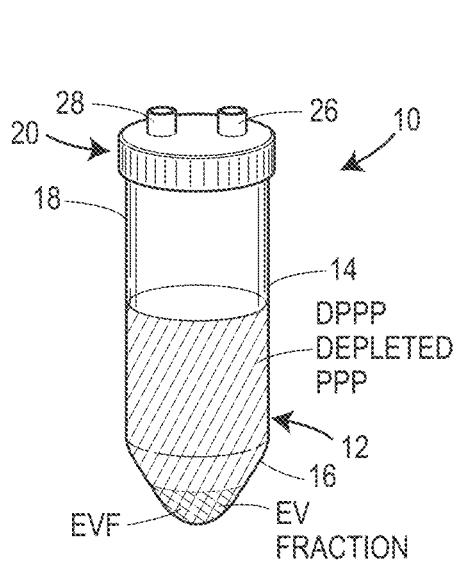
Figure 3D:
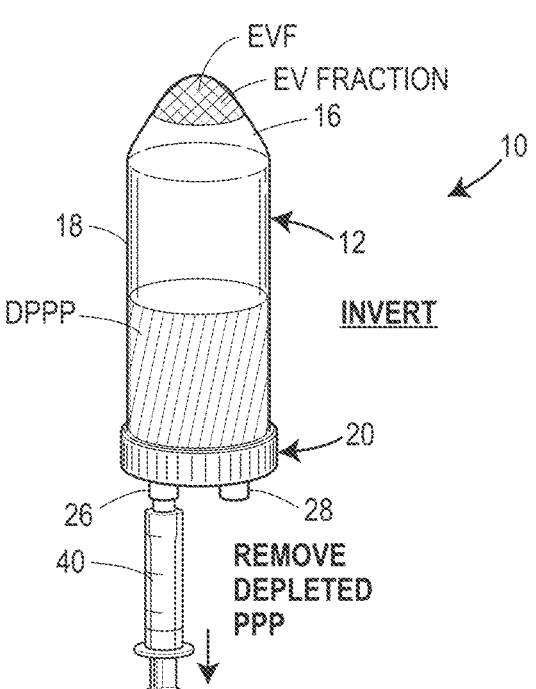

So configured, and explained more below relative to FIGS. 3A-3G, for example, the container 12 is moveable between an upright position, such as depicted in FIG. 1, and an inverted position, such as depicted in FIG. 3D. The upright position is a position in which fluid, such as a biofluid including platelet-poor plasma, disposed in the container 12 is centrifuged to precipitate at least one extracellular vesicle separate from the fluid disposed in the container 12. The inverted position is a position in which one or more of the fluid having the at least one extracellular vesicle depleted therefrom is removed from the container 12 and platelet-rich plasma mixed with the at least one extracellular vesicle removed from the platelet-poor plasma is withdrawn from the container 12 through the at least one port 24 of the cap 20 for injection.

Still referring to FIG. 1, in one example the at least one port 24 of the cap 20 includes a first port 26 configured to receive or transmit air and having a filter 27. The at least one port 24 further includes a second port 28 configured to receive or transmit fluid, such as biofluid, as explained more below. In addition, each of the first and second ports 26, 28 may include a removable cap 30, and the second port 28 configured to receive or transmit fluid may include a luer lock connection 32 configured to be coupled to a syringe.

As further depicted in FIG. 1, the first end 16 of the container 12 may include a tapered portion 34 and the second end 18 may be an open end, such as when the cap 20 is removed from the second end 18.

Figure 2:
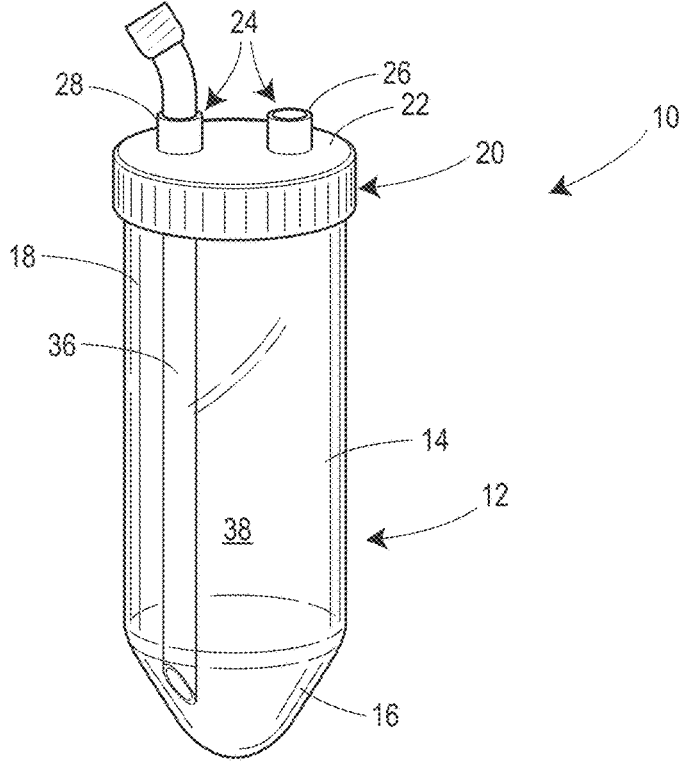
FIG. 2 is the device of the FIG. 1 with tubing coupled thereto.

Referring now to FIG. 2, the centrifugal device 10 may further include at least one tube 36 disposed in the second port 28 and extending into an internal area 38 of the container 12. The at least one tube 36 is configured to aid in the addition or removal of fluid, such as biofluid, to or from the container 12.

Referring now to FIGS. 3A-3G, steps of a method of isolating extracellular vesicles from fluid using the centrifugal device 10 of one or more FIGS. 1 and 2, for example, are depicted. Referring first to FIG. 3A, the method first includes adding an aqueous two-phase solution to the container 12 of the centrifugal device 10 through the first port 26 disposed at the second end 18 of the body 12 of the container 12, such as via a syringe 40. The container 12 is depicted in the upright position in FIGS. 3A and 3B. In this example, the aqueous two-phase solution is a concentrated aqueous two-phase solution including a concentrated polyethylene glycol-dextran (PEG-DEX) solution. The aqueous two-phase solution is required for the purification of biological materials. In addition, the aqueous two-phase solution may be referred to as the SuperShot™ solution of Forever Labs, Inc. It will be appreciated that the aqueous two-phase solution may include other aqueous polymers and still fall within the scope of the present disclosure. In addition, and in some examples, the container 12 may be made of one of polypropylene and/or polystyrene and is coated with a hydrophobic layer. During use, it was determined that the container 12 made of polystyrene had the lowest residual aqueous two-phase solution. Because minimizing residual aqueous two-phase solution, such as PEG-DEX, is desirable in preparing the platelet-rich plasma with extracellular vesicles for injection, having the container 12, e.g., centrifuge tube, made from polystyrene may be optimal.

In addition, and referring to FIG. 3B, the method further includes adding a fluid, such as platelet-poor plasma, to the container 12 of the centrifugal device 10 also through the first port 26 disposed at the second end 18 of the container 12 and by way of the syringe 40, for example. In one example, the platelet-poor plasma that is added to the container 12 is created after first centrifuging the platelet-rich plasma. Specifically, after centrifugation of the platelet-rich plasma, a portion of the platelet-poor plasma is aseptically removed and then combined with the aqueous two-phase solution in the container 12 of the centrifugal device 10. The platelet-rich plasmas may be centrifuged using the centrifugal device 10 of the present disclosure or any other centrifugation device or system 11 (see, e.g., FIG. 3B) commonly known to a skilled person.

In addition, in another example, while the aqueous two-phase solution and the fluid, such as the platelet-poor plasma referred to above, are being added to the container 12 via the first port 26, air is allowed to simultaneously exit the second port 28 of the cap 20 disposed at the second end 18 of the body 14 of the container 12. The aqueous two-phase solution, such as the PEG-DEX solution, added to the plasma enables the precipitation of small low-density molecules, under centrifugation, including extracellular vesicles.

After the platelet-poor plasma is added to the container 12 having the two-phase aqueous solution AS disposed therein, the method further includes mixing and centrifuging the aqueous two-phase solution and the platelet-poor plasma in the container 12, such as using the centrifugal device 10 and the centrifugation system 11 of FIG. 3B. Upon doing so, a fraction of low-density biomolecules including extracellular vesicles (FEV) is formed and concentrated one or more of near or at the first end 16 of the container 12, as depicted in FIG. 3C. The fraction of extracellular vesicles is separate from the platelet-poor plasma and/or depleted or removed from the platelet-poor plasma (PPP), as also depicted in FIG. 3C. In addition, in another example, centrifuging the aqueous two-phase solution and platelet-poor plasma in the container 12 to form the fraction of extracellular vesicles disposed near the first end 18 of the container 12 separate from the platelet-poor plasma may include removing the fraction of extracellular vesicles from the platelet-poor plasma and forming the fraction of extracellular vesicles disposed near the first end 18 of the container 12 separate from the platelet-poor plasma in the container 12, as also depicted in FIG. 3C.

Referring now to FIG. 3D, the method further includes moving the container 12 of the centrifugal device 10 from an upright position, as depicted in FIG. 3A for example, to an inverted position, as depicted in FIG. 3D. Once in the inverted position, the method further includes removing the platelet-poor plasma with the fraction of extracellular vesicles depleted therefrom and the aqueous two-phase solution from the container 12 through the at least one port 24 of the cap 20, such as the first port 26 depicted in FIG. 3D. In this example, the platelet-poor plasma with the fraction of extracellular vesicles depleted therefrom is removed from the container 12 via the syringe 40, and the second port 28 receives air that flows into the container 12. However, it will be understood the platelet-poor plasma with the fraction of extracellular vesicles depleted therefrom may be removed from the container 12 through the first port 26 using another device different from the syringe 40, such as the tubing 36 of FIG. 2, and still fall within the scope of the present disclosure.

Referring now to FIG. 3E, the method further includes moving the container 12 back to the upright position, as depicted in FIG. 3E, and adding platelet-rich plasma (PRP) to the container 12 having the fraction of extracellular vesicles. The method further includes mixing the platelet-rich plasma with the fraction of extracellular vesicles disposed near the first end 16 of the container 12, resuspending the extracellular vesicles in the platelet-rich plasma. In one example, moving the container 12 of the centrifugal device 10 back to the upright position and adding platelet-rich plasma to the container 12 comprises adding platelet-rich plasma through the first port 26 of the cap 20 disposed on the second end 18 of the container 12 while the fraction of the extracellular vesicles removed from the platelet-poor plasma is disposed near the first end 16 of the container 12.

Referring now to FIG. 3F, the method still further includes moving the container 12 of the centrifugal device 10 back to the inverted position and removing the platelet-rich plasma (PRP) with the fraction of extracellular vesicles (EVF) mixed therein through the at least one port 24, such as the first port 26 of the cap 20, via the syringe 40 for injection. In one example, the platelet-rich plasma with the fraction of extracellular vesicles (EVF) one or more of mixed or disposed therein is referred to as SuperShot™ PRP.

Figure 3G:
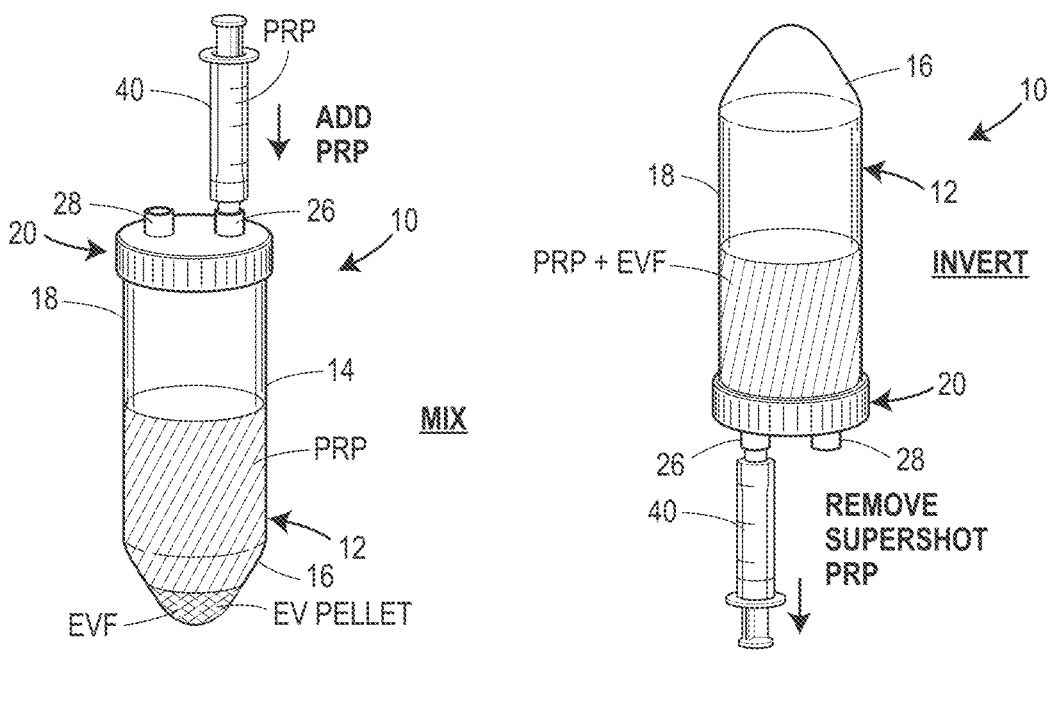
Figure 3G:
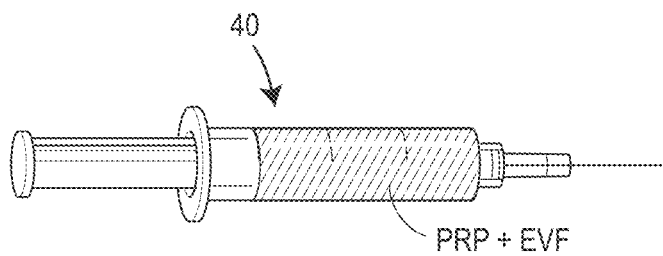

Referring now to FIG. 3G, the syringe 40 is depicted having the platelet-rich plasma with the fraction of the extracellular vesicles (EVF) centrifuged from the platelet-poor plasma and aqueous two-phase solution mixture, as described above, disposed therein and ready for injection. While the syringe 40 is depicted, it will be understood that another injection or drug administration device or system may alternatively and/or additionally be used and still fall within the scope of the present disclosure.

Figure 4:
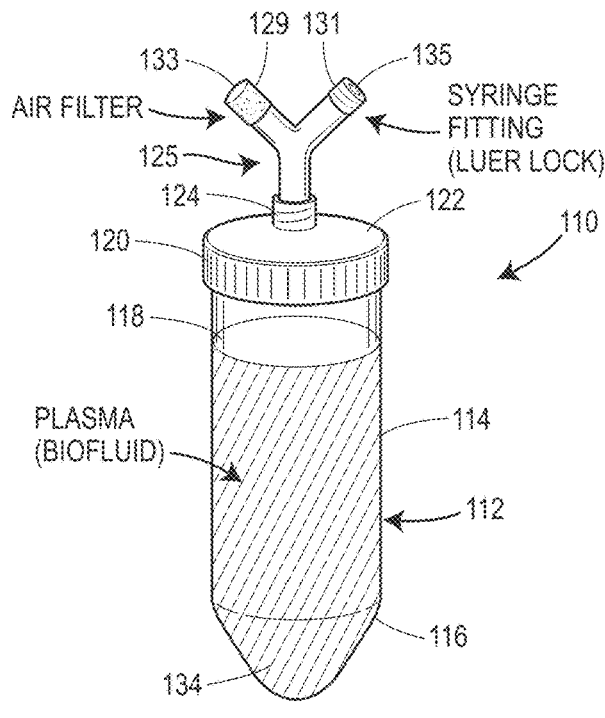
FIG. 4 is a front perspective view of another centrifugal device according to another aspect of the present disclosure.
Figure 5:
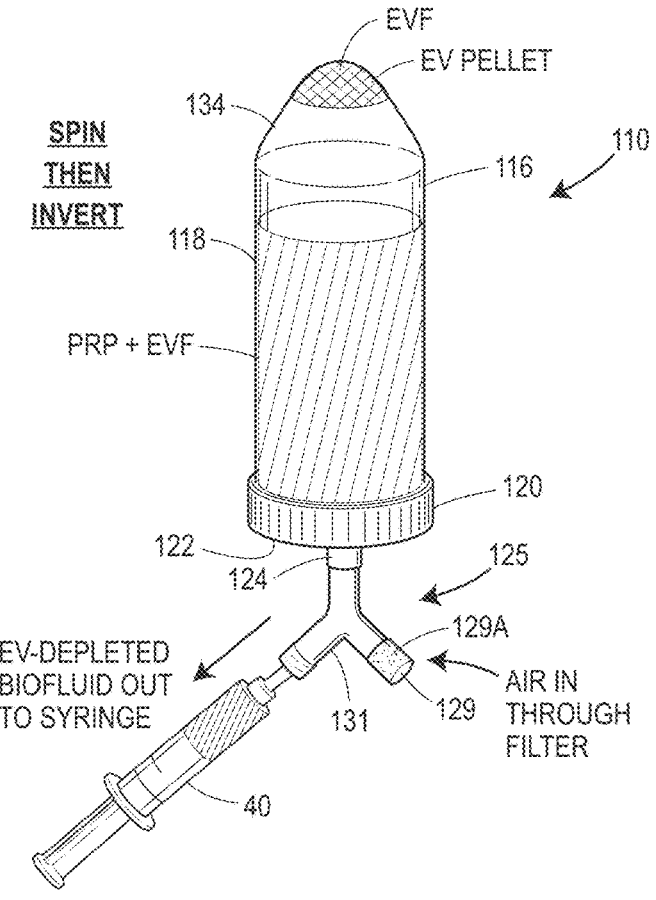
FIG. 5 is an inverted view of the device of FIG. 4.

Referring now to FIGS. 4 and 5, another centrifugal device 110 according to another aspect of the present disclosure is depicted. The centrifugal device 110 includes many of the same features as the centrifugal device 10 of FIGS. 1-3G, but instead of the cap 20 having the first port 26 and the second port 28 of the centrifugal device 10, the centrifugal device 110 includes a cap having only a single port with a Y-shaped connector coupled thereto, as explained more below. Parts of the centrifugal device 110 that are the same as parts of the centrifugal device 10 are numbered 100 more and are not explained again here for the sake of brevity. As will be appreciated at least in view of the description below, the centrifugal device 110 may also operate according to the method described above and depicted in FIGS. 3A-3G. Said another way, each of the centrifugal devices 10, 110 of the present disclosure may be used to employ the method of isolating extracellular vesicles described above. It will be appreciated that the centrifugal device 110 may take the place of the centrifugal device 10 depicted in FIGS. 3A-3G and employ the method just as effectively as the centrifugal device 10, for example.

Referring now to FIG. 4, the centrifugal device 110 includes a container 112, which may take the form of a tube and/or be cylindrical in shape. The container 112 includes a body 114 having a first end 116 and a second end 118 disposed opposite to the first end 116. A cap 120 is removably coupled to the second end 18 of the container 112 and includes a top surface 122 having a port 124 configured to receive or transmit one or more of fluid, such as a biofluid, or air, as explained more below.

In addition, a Y-connector 125 is removably coupled to the port 124 of the cap 120 and has a first portion 129, such as a first port, for receiving or transmitting air and having a filter 129A (FIG. 5A), and a second portion 131, such as a second port, for receiving or transmitting fluid, such as biofluid.

So configured, and like the centrifugal device 10 and method depicted in FIGS. 3A-3G, for example, the container 112 is moveable between an upright position, such as depicted in FIG. 4, and an inverted position, such as depicted in FIG. 5. The upright position is a position in which fluid, such as a biofluid including platelet-poor plasma, disposed in the container 112 is centrifuged to precipitate at least one extracellular vesicle separate from the fluid disposed in the container 112. The inverted position is a position in which the fluid having the at least one extracellular vesicle depleted therefrom is removed from the container 112 through the second port 131 of the Y-connector 125. The inverted position is additionally and/or alternatively a position in which the platelet-rich plasma mixed with the at least one extracellular vesicle removed from the platelet-poor plasma is withdrawn from the container 112 through the port 124 of the cap 120 and the second port 131 of the Y-connector 125 for injection. Further, the first portion 129, such as the first port, may receive air when the container 112 is in the inverted position, as depicted in FIG. 5.

In addition, each of the first and second ports 129, 131 may include a removable cap 133 (FIG. 4), and the second port 131 configured to receive or transmit fluid may include a syringe fitting 135 (FIG. 4), such as a luer lock connection, configured to be coupled to a syringe.

As further depicted in FIGS. 4 and 5, the first end 116 of the container 112 may include a tapered portion 134 and the second end 118 may be an open end, such as when the cap 120 is removed from the second end 118. While the first end 116 of the container 112 is depicted having the tapered portion 134 in FIGS. 4 and 5, the first end 116 may alternatively include a shape different from a tapered portion, such as a flat portion, and still fall within the scope of the present disclosure.

Figure 6A:
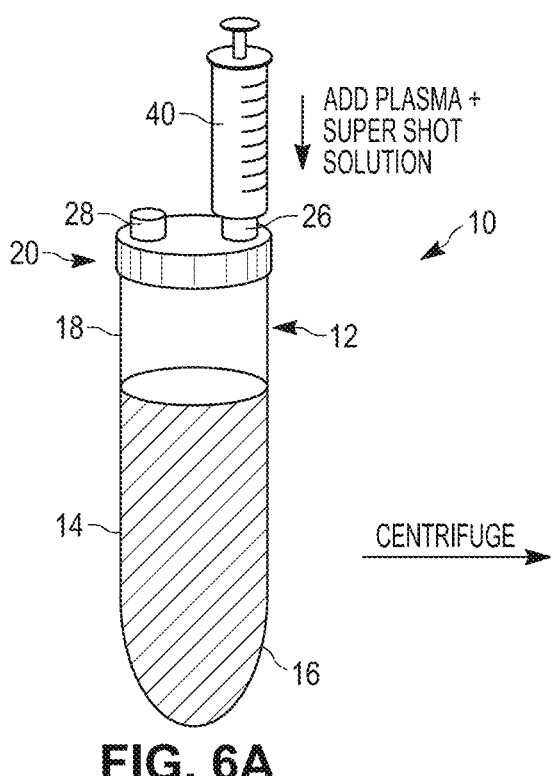
FIGS. 6A-6E depict steps of another method of isolation of extracellular vesicles according to yet another aspect of the present disclosure.

Referring now to FIGS. 6A-6E, another method of isolating extracellular vesicles from a fluid using the centrifugal device 10 of one or more of FIGS. 1 and 2, for example, is depicted. Referring first to FIG. 6A, the method includes transferring a first volume of plasma from a transfer device, such as the syringe 40, to the container 12 of the centrifugal device 10, leaving a second volume of plasma in the transfer device 40. In this example, and as depicted in FIG. 6A, the container 12 of the centrifugal device 10 is in an upright position. The method further includes maintaining the second volume of plasma in the transfer device 40, which is later used for injection as explained more below.

More generally, and in one example, the second volume of plasma maintained in the transfer device 40 is equal to a desired volume of a final injection. Thus, if a user, such as a physician, desires to inject 5 mL of platelet-rich plasma and has 20 mL of plasma, the physician adds 15 mL of plasma to the container 12 of the centrifugal device 10 and retains 5 mL of plasma in the transfer device 40, such as the transfer syringe 40. As such, in this example, the first volume of plasma transferred from the transfer device 40 to the container 12 is 15 mL of plasma, and the second volume of plasma maintained in the transfer device 40 is 5 mL. It will be appreciated that various other combinations of first and second volumes of plasma may alternatively be desired and, thus, selected by a user and/or physician, enabling flexibility and ease of injection volume, for example, and still fall within the scope of the present disclosure. In addition, it will also be appreciated that various other types of transfer devices different from the transfer device 40, e.g., the syringe 40, may alternatively and/or additionally be used and again still fall within the scope of the present disclosure.

In addition, in one example, before transferring the first volume of plasma from the transfer device 40 to the container 12 of the centrifugal device 10, the method may also comprise adding whole blood to a container of another centrifugal device, such as a second centrifugal device (not shown). In this example, the centrifugal device 10 of FIG. 6A is a first centrifugal device 10. The method then also includes centrifuging the whole blood, and removing the red blood cells from the container of the second centrifugal device. The plasma from the container of the second centrifugal device is then transferred to the transfer device 40, such as the syringe 40, after removing the red blood cells.

Still referring to FIG. 6A, the method next includes adding the aqueous two-phase solution to the container 12 of the centrifugal device 10, such as via the at least one port 26 of the container 12. In this way, the aqueous two-phase solution is combined with the plasma transferred from the transfer device 40. In some examples, air is simultaneously allowed to exit the container 14, such as through the second port 28, while the aqueous two-phase solution is being added to the container 12. In this example, the aqueous two-phase solution is again a concentrated aqueous two-phase solution including a concentrated polyethylene glycol-dextran (PEG-DEX) solution. As noted above, the aqueous two-phase solution is required for the purification of biological materials and may be referred to as the SuperShot™ solution of Forever Labs, Inc. It will be appreciated that the aqueous two-phase solution may include other aqueous polymers and still fall within the scope of the present disclosure.

The method further includes centrifuging the aqueous two-phase solution and the plasma in the container 12 to form a fraction of extracellular vesicles and platelet-rich plasma. In one example, and as depicted in FIG. 6B, the fraction of extracellular vesicles and platelet-rich plasma is disposed near the first end 16 of the container 12 of the centrifugal device 10 separate from the platelet-poor plasma and the remaining aqueous two-phase solution.

Figure 6B:
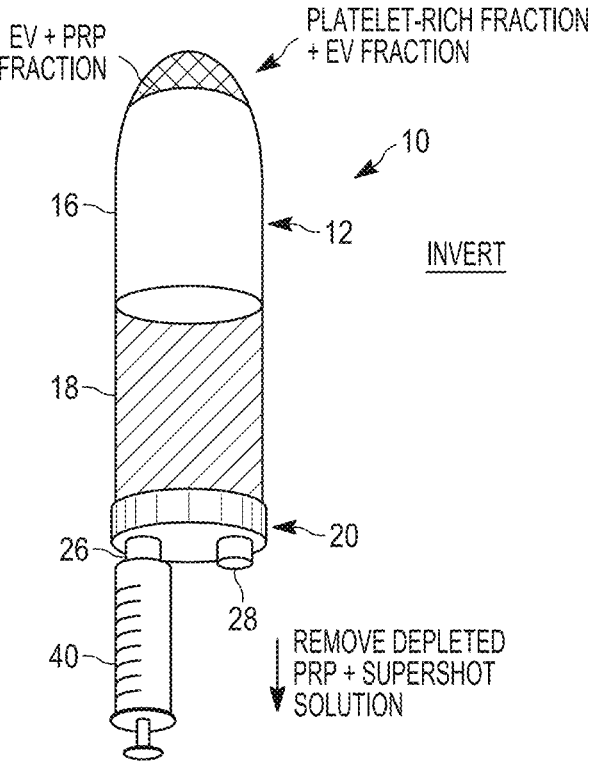

Referring now to FIG. 6B, the method further includes inverting the container 12 of the centrifugal device 10 and removing the remaining aqueous two-phase solution and depleted platelet-poor plasma from the container 12. In one example, inverting the container 12 of the centrifugal device 10 and removing the remaining aqueous two-phase solution and depleted platelet-poor plasma from the container 12 comprises removing the remaining aqueous two-phase solution and depleted platelet-poor plasma from the container 12 through the first port 26 via the transfer device 40, such as the syringe 40, while air flows into the second port 28 of the container 12.

Figure 6C:
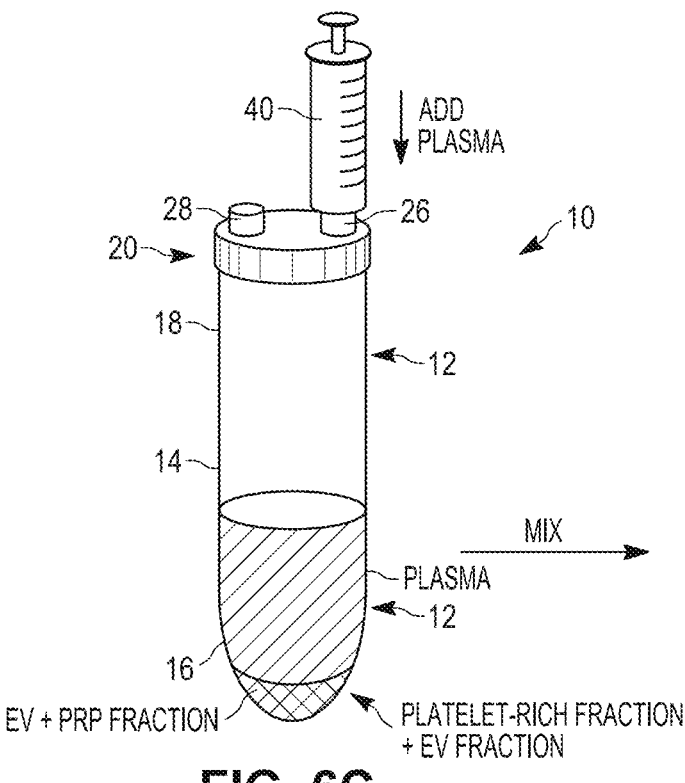

Referring now to FIG. 6C, the method still further includes moving the container 12 from an inverted position (FIG. 6B) back to an upright position and adding the second volume of plasma maintained in the transfer device 40, such as the syringe 40, into the container 12 of the centrifugal device 10. In one example, moving the container 12 from an inverted position back to an upright position and adding the second volume of plasma maintained in the transfer device 40 into the container 12 of the centrifugal device 10 comprises adding the second volume of plasma from the transfer device 40 through the first port 26 disposed on the second end 18 of the container 12 while the fraction of extracellular vesicles and platelet-rich plasma is disposed at or near the first end 16 of the container 12, as depicted in FIG. 6C. The method still further includes resuspending the fraction of extracellular vesicles and platelet-rich plasma with the second volume of plasma in the container 12 by one or more of shaking, inverting, vortexing, and/or centrifuging the container 12, for example.

Figure 6D:
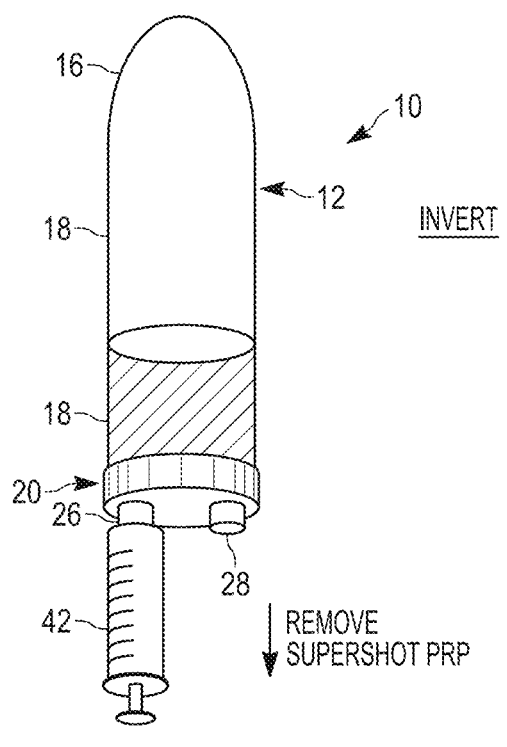
Figure 6E:
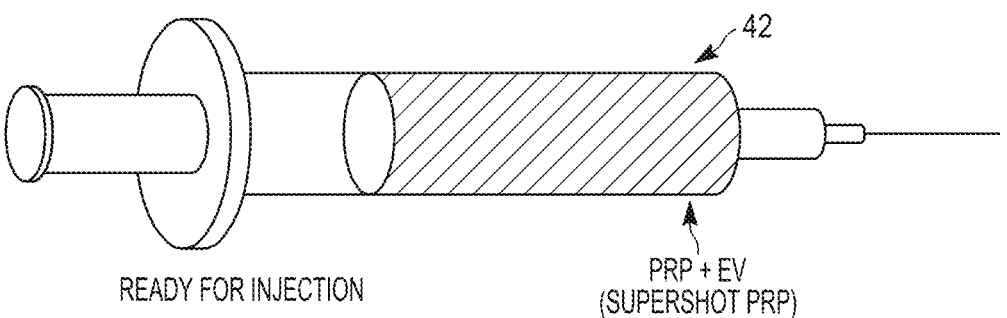

Referring now to FIG. 6D, the method also includes inverting the container 12 and removing the platelet-rich plasma with extracellular vesicles for placement in an injection device 42, such as an injection syringe 42 (see also FIG. 6E). The volume of platelet-rich plasma and extracellular vesicles is equal to the second volume of plasma in the transfer device 40. In one example, inverting the container 12 and removing the platelet-rich plasma with extracellular vesicles for placement in the injection device 42 comprises removing platelet-rich plasma with the extracellular vesicles through the first port 26 of the container 12 via the injection syringe 42. In another example, inverting the container 12 and removing the platelet-rich plasma with extracellular vesicles for placement in an injection device 42 comprises removing platelet-rich plasma with extracellular vesicles through a port of the Y-connector 125 (see, e.g., FIGS. 4 and 5) coupled to the first port 26 of the container 12 of the centrifugal device 10 via the injection syringe 42.

At least in view of the foregoing, it will be understood that the centrifugal devices 10, 110 and method of isolating extracellular vesicles of the present disclosure include several advantages. For example, the method and devices 10, 110 reduce the amount of remaining extracellular vesicles after a platelet rich plasma injection, for example. In addition, the method and devices 10, 110 of the present disclosure also increase the overall concentration of extracellular vesicles within the platelet-rich plasma, improving the overall therapeutic effects of the platelet-rich plasma.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Some implementations may be described using the expression "coupled" along with its derivatives. For example, some implementations may be described using the term "coupled" to indicate that two or more elements are in direct physical or electrical contact. The term "coupled," however, may also mean that two or more elements are not in direct contact with each other, but yet still co-operate or interact with each other. The implementations are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the implementations herein. This is done merely for convenience and to give a general sense of the invention. This description should be read to include one or at least one and the singular also includes the plural unless it is obvious that it is meant otherwise.

Further, while particular implementations and applications have been illustrated and described, it is to be understood that the disclosed implementations are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

We claim:

1. A method of isolating extracellular vesicles, the method comprising:

adding an aqueous two-phase solution and a first fluid to a container of a centrifugal device, the container in an upright position;

centrifuging the aqueous two-phase solution and the first fluid in the container to form a fraction of extracellular vesicles disposed near a first end of the container separate from the first fluid;

moving the container of the centrifugal device from an upright position to an inverted position and removing the first fluid with the fraction of extracellular vesicles depleted therefrom from the container through at least one port of the container;

moving the container back to the upright position and adding a second fluid to the container;

mixing the second fluid with the fraction of extracellular vesicles disposed near the first end of the container; and moving the container back to the inverted position and removing the second fluid with the fraction of extracellular vesicles through the at least one port of the container for injection.

2. The method of claim 1, further comprising centrifuging a platelet-rich plasma and aseptically removing a portion of platelet-poor plasma from the platelet-rich plasma before adding the aqueous two-phase solution and the first fluid to a container of the centrifugal device.

3. The method of claim 1, wherein adding an aqueous two-phase solution and a first fluid to a container of a centrifugal device comprises adding a concentrated polyethylene glycol-dextran (PEG-DEX) solution and a platelet-poor plasma as the aqueous two-phase solution; and wherein the aqueous two-phase solution and the first fluid are added to the container as via at least one port disposed at a second end of the container of the centrifugal device.

4. The method of claim 3, wherein adding the aqueous two-phase solution and the first fluid to the container via at least one port disposed at the second end of the container of the centrifugal device comprises adding the aqueous two-phase solution and platelet-poor plasma to the container via a first port of the container and allowing air to simultaneously exit through a second port of the container.

5. The method of claim 1, wherein centrifuging the aqueous two-phase solution and the first fluid in the container to form a fraction of extracellular vesicles comprises removing the fraction of extracellular vesicles from platelet-poor plasma and forming the fraction of extracellular vesicles disposed near the first end of the container separate from the platelet-poor plasma in the container.

6. The method of claim 1, wherein adding a second fluid to the container of moving the container back to the upright position and adding a second fluid to the container further comprises adding platelet-rich plasma through a first port disposed on a second end of the container.

7. The method of claim 1, wherein removing the second fluid with the fraction of extracellular vesicles through the at least one port of the container for injection of moving the container back to the inverted position and removing the second fluid with the fraction of extracellular vesicles through the at least one port of the container for injection further comprises one or more of: (1) removing platelet-rich plasma with the fraction of extracellular vesicles through a first port of the container via a syringe for injection; or (2) removing platelet-rich plasma with the fraction of extracellular vesicles through a port of a Y-connector coupled to the at least one port of the container of the centrifugal device via a syringe for injection.

8. A method of isolating extracellular vesicles from a fluid, the method comprising:

transferring a first volume of plasma from a transfer device to a container of a centrifugal device, maintaining a second volume of plasma in the transfer device;

adding an aqueous two-phase solution to the container of the centrifugal device;

centrifuging the aqueous two-phase solution and the first volume of plasma in the container to form a fraction of extracellular vesicles and platelet-rich plasma;

inverting the container of the centrifugal device and removing remaining aqueous two-phase solution and depleted platelet-poor plasma from the container;

moving the container from an inverted position back to an upright position and adding the second volume of plasma from the transfer device into the container of the centrifugal device;

resuspending the fraction of extracellular vesicles and platelet-rich plasma with the second volume of plasma in the container by one or more of shaking, inverting, vortexing, and/or centrifuging the container; and inverting the container and removing platelet-rich plasma with extracellular vesicles for placement in an injection device, the volume of platelet-rich plasma and extracellular vesicles equal to the second volume of plasma in the transfer device.

9. The method of claim 8, wherein the centrifugal device is a first centrifugal device, and, before transferring the first volume of plasma from the transfer device to the container of the first centrifugal device, the method further comprises adding whole blood to a container of a second centrifugal device, centrifuging the whole blood, and removing red blood cells from the container of the second centrifugal device.

10. The method of claim 9, further comprising transferring the second volume of plasma from the container of the second centrifugal device to the transfer device after removing the red blood cells from the container of the second centrifugal device.

11. The method of claim 8, wherein adding an aqueous two-phase solution to the container of the centrifugal device comprises adding a concentrated polyethylene glycol-dextran (PEG-DEX) solution as the aqueous two-phase solution; and wherein the aqueous two-phase solution is added to the container via at least one port of the container.

12. The method of claim 11, wherein the aqueous two-phase solution is added to the container via at least one port of the container comprises wherein the aqueous two-phase solution is added to the container via a first port of the container and air is allowed to simultaneously exit through a second port of the container.

13. The method of claim 8, wherein centrifuging the aqueous two-phase solution and the plasma in the container comprises centrifuging the aqueous two-phase solution and the plasma in the container to form the fraction of extracellular vesicles and platelet-rich plasma disposed near a first end of the container.

14. The method of claim 8, wherein removing remaining aqueous two-phase solution and depleted platelet-poor plasma from the container of inverting the container of the centrifugal device and removing remaining aqueous two-phase solution and depleted platelet-poor plasma from the container comprises removing the remaining aqueous two-phase solution and depleted platelet-poor plasma from the container through a first port of the container via a.

15. The method of claim 8, wherein adding the second volume of plasma from the transfer device into the container of the centrifugal device of moving the container from an inverted position back to an upright position and adding the second volume of plasma from the transfer device into the container of the centrifugal device comprises adding the second volume of plasma from the transfer device and through a first port disposed on a second end of the container.

16. The method of claim 8, wherein removing platelet-rich plasma with extracellular vesicles for injection of inverting the container and removing platelet-rich plasma with extracellular vesicles for injection comprises one or more of: (1) removing platelet-rich plasma with extracellular vesicles through a first port of the container via a syringe for injection; or (2) removing platelet-rich plasma with extracellular vesicles through a port of a Y-connector coupled to the at least one port of the container of the centrifugal device via a syringe for injection.

17. A method of isolating extracellular vesicles from a fluid, the method comprising:

transferring a first volume of plasma from a transfer device to a container of a centrifugal device;

adding an aqueous two-phase solution to the container;

centrifuging the aqueous two-phase solution and the first volume of plasma in the container to form a fraction of extracellular vesicles and platelet-rich plasma;

inverting the container of the centrifugal device and removing remaining aqueous two-phase solution and depleted platelet-poor plasma from the container;

moving the container to an upright position and adding a second volume of plasma from the transfer device into the container;

resuspending the fraction of extracellular vesicles and platelet-rich plasma with the second volume of plasma in the container; and inverting the container and removing platelet-rich plasma with extracellular vesicles for placement in an injection device.

* * * * *